(12) United States Patent
Tanaami et al.

(10) Patent No.: US 7,978,327 B2
(45) Date of Patent: Jul. 12, 2011

(54) MOLECULARITY MEASUREMENT INSTRUMENT AND MOLECULARITY MEASUREMENT METHOD

(75) Inventors: Takeo Tanaami, Musashino (JP); Hidetoshi Aoki, Musashino (JP); Saya Satou, Musashino (JP); Yumiko Sugiyama, Musashino (JP)

(73) Assignee: Yokogawa Electric Corporation, Tokyo (JP)

( * ) Notice: Subject to any disclaimer, the term of this patent is extended or adjusted under 35 U.S.C. 154(b) by 186 days.

(21) Appl. No.: 12/365,280

(22) Filed: Feb. 4, 2009

(65) Prior Publication Data

US 2009/0201506 A1    Aug. 13, 2009

(30) Foreign Application Priority Data

Feb. 8, 2008   (JP) .................................. 2008-028930

(51) Int. Cl.
*G01B 9/08*   (2006.01)
(52) U.S. Cl. ....................................... 356/392
(58) Field of Classification Search ................... 356/392
See application file for complete search history.

(56) References Cited

U.S. PATENT DOCUMENTS

| 5,528,046 A * | 6/1996 | Ishikawa .................... 250/461.2 |
| 2004/0051051 A1* | 3/2004 | Kato et al. ................... 250/458.1 |
| 2004/0113096 A1 | 6/2004 | Tanaami et al. |

FOREIGN PATENT DOCUMENTS

JP   2004-191232 A   7/2004

OTHER PUBLICATIONS

Guilbault, George G., "Practical Fluorescence" Theory, Methods and Techniques; Marcel Derrer, Inc., New York 1973, pp. 1-78.

* cited by examiner

*Primary Examiner* — Roy Punnoose
(74) *Attorney, Agent, or Firm* — Westerman, Hattori, Daniels & Adrian, LLP

(57) ABSTRACT

There is provided a molecularity measurement instrument capable of working out the number of molecules in a sample by comparing a measured value of a light quantity with a theoretical light quantity per a single molecule, and a molecularity measurement method using the same. The molecularity of the sample is quantitatively estimated on the basis of a light quantity having correlation with the molecularity. The molecularity measurement method comprises the step of working out a theoretical light quantity per a single molecule, the step of measuring a light quantity of the sample by use of an image detector, and the step of working out the molecularity of the sample on the basis of a ratio of the light quantity of the sample to the theoretical light quantity as worked out.

7 Claims, 6 Drawing Sheets

FIG. 2
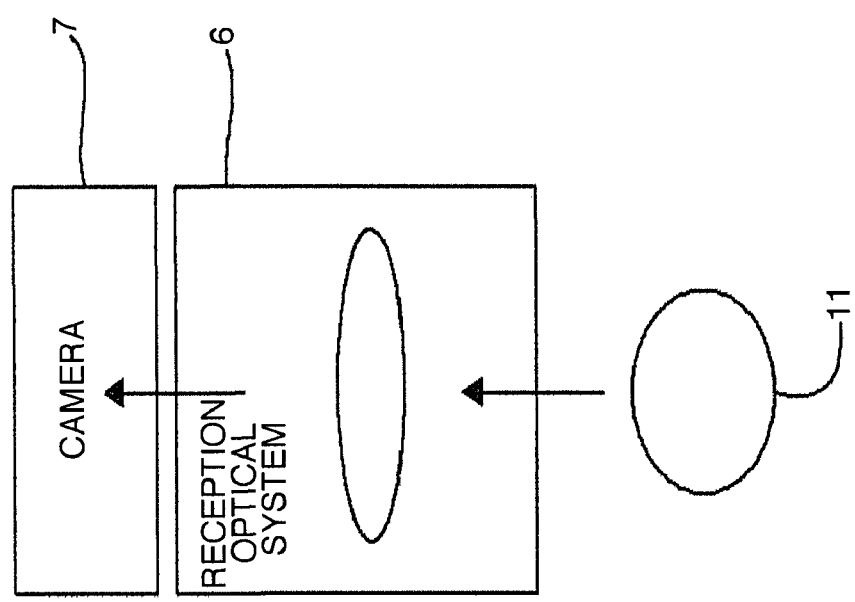
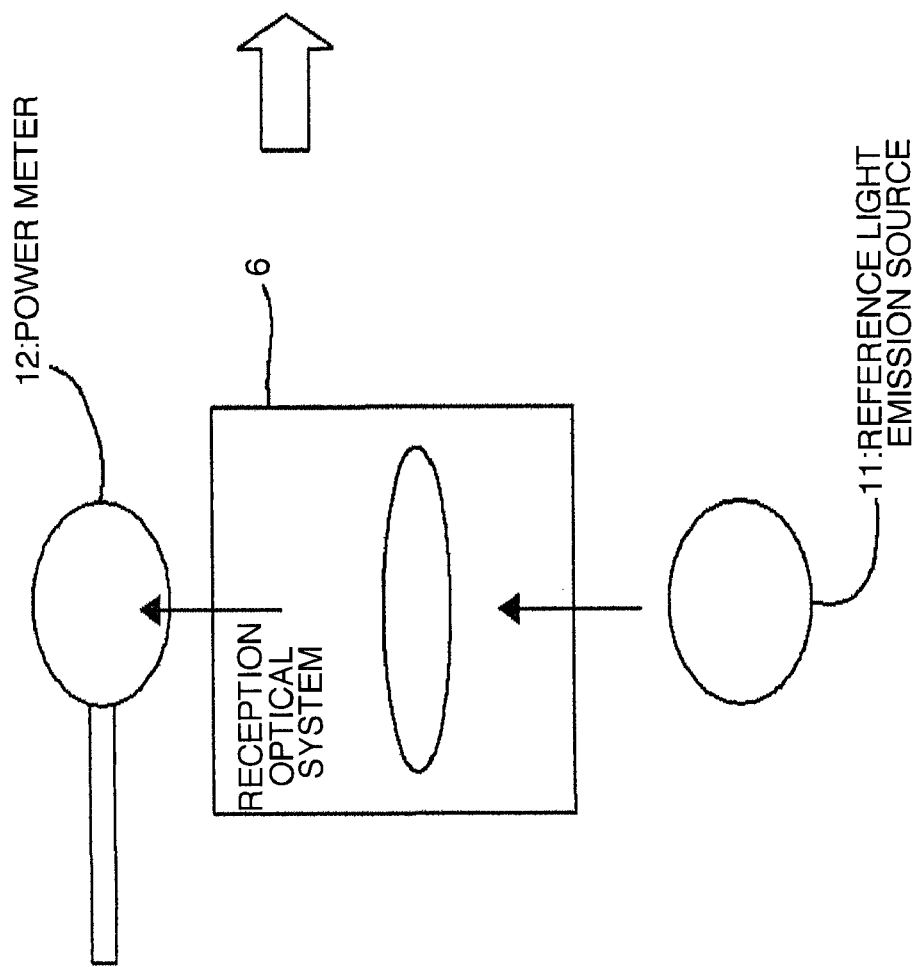

FIG. 3
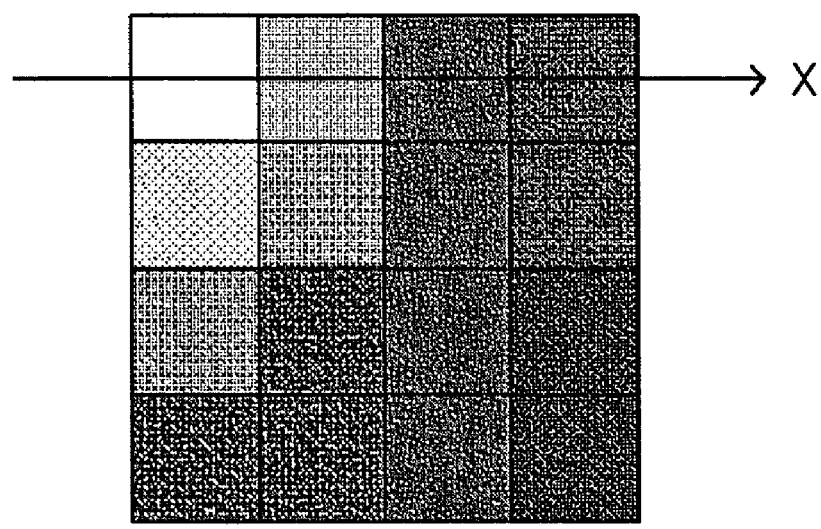
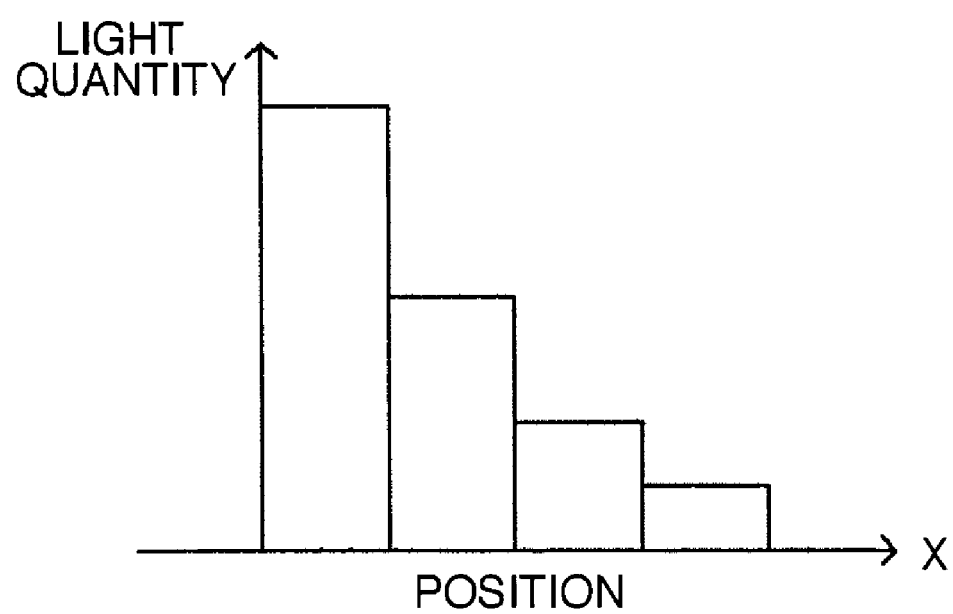

MOLECULARITY MEASUREMENT INSTRUMENT AND MOLECULARITY MEASUREMENT METHOD

FIELD OF THE INVENTION

The present invention relates to a molecularity measurement instrument for quantitatively measuring molecularity (the number of molecules) of a sample on the basis of a light quantity having correlation with the molecularity, and a molecularity measurement method using the same.

BACKGROUND OF THE INVENTION

A micro-array scanner is well known as an apparatus for reading DNA micro-array. By capturing an image of DNA micro-array while scanning the image with the use of a micro-array scanner, it is possible to measure fluorescent light quantity distribution of a target molecule, in the form of a two-dimensional image.
[Patent Document 1] JP 2004-191232 A

SUMMARY OF THE INVENTION

With the micro-array scanner, however, a fluorescent light quantity is measured with a PMT (photomultiplier) while amplifying current, so that it is difficult to obtain correlation between the fluorescent light quantity, and an excitation light quantity irradiated on a sample. Accordingly, fluorescence intensity is generally expressed on an optional unit basis. Further, since the micro-array scanner does not have means for correcting measurement conditions for excitation light, and so forth, it is not possible to make direct comparison between data blocks obtained in respective measurements taken a plurality of times, and in respective measurements taken by use of a plurality of apparatuses although relative measurements within one screen can be taken.

On one hand, uniform light quantity, such as light quantity of excitation light and so forth, can be measured so as to be traceable to the national standard by use of a photodiode, and so forth, however, in this case, nothing but data on a point in zero dimension, other than an image, can be obtained.

On the other hand, a method for calibrating a luminance value of a camera on the basis of optical power (w) according to the national standard has been disclosed in JP 2004-191232A. With the use of the method, it is possible to obtain a light quantity value of optical power traceable to the national standard by the pixel of an image picked up (hereinafter referred to as "an image power meter"). However, a specific method for molecular count calculation has not been described therein. Further, there has been disclosed only a descriptive formula concerning absorption, but calculation formulas concerning emission light, fluorescent light, and a measurement system, respectively, have not been disclosed.

It is therefore an object of the invention to provide a molecularity measurement instrument capable of working out the number of molecules in a sample by comparing a measured value of a light quantity with a theoretical light quantity per a single molecule, and a molecularity measurement method using the same. More specifically, it is possible to attain, for example, the following objects:

(1) To show a specific method enabling comparison between a plurality of measurements, and between a plurality of bodies of measuring instruments, whereby evaluation on fluorescent light quantity, and so forth is carried out on the basis of an absolute value having a light quantity unit although such evaluation has been possible only on a relative basis in the past.

(2) To show a specific method for estimating the number of molecules (molecularity) present in a sample on the basis of a light quantity from a sample (fluorescent light, emission light, optical absorption), and predetermined measurement conditions (3) To show a specific method for measuring spatial distribution of fluorescence molecularity on a sample by similarly estimating molecularity by the pixel of an image through combined use of the method disclosed in JP 2004-191232A described as above because it is possible to obtain not only information on a point in zero dimension but also a light quantity on a pixel-by-pixel basis directly from a camera image in two-dimensions.

The invention provides in its first aspect a molecularity measurement method for quantitatively measuring molecularity of a sample on the basis of a light quantity having correlation with the molecularity, said method comprising the step of working out a theoretical light quantity per a single molecule, the step of measuring a light quantity of the sample by use of an image detector, and the step of working out the molecularity of the sample on the basis of a ratio of the light quantity of the sample to the theoretical light quantity as worked out.

With the molecularity measurement method, the molecularity of the sample is worked out on the basis of the ratio of the light quantity of the sample, as measured, to the theoretical light quantity as worked out, so that it is possible to derive the molecularity of the sample directly from the light quantity of the sample, the molecularity thereof being measured.

The molecularity measurement method may further comprise the step of calibrating corresponding relationship between a light quantity of the image detector, and an output value thereof, and in the step of measuring the light quantity of the sample, the light quantity of the sample may be measured by use of the corresponding relationship as calibrated.

The light quantity having the correlation with the molecularity may be a fluorescent light quantity of fluorescence emitted from the sample, and in the step of working out the theoretical light quantity, a theoretical fluorescent light quantity may be worked out as the theoretical light quantity by use of molar absorption coefficient, quantum efficiency, excitation wavelength efficiency, and a excitation light quantity.

The light quantity having the correlation with the molecularity may be an optical absorption quantity by the sample.

The light quantity having the correlation with the molecularity may be an emission light quantity.

The image detector may comprise a confocal optical system.

Further, the invention provides in its second aspect a molecularity measurement instrument for quantitatively measuring molecularity of a sample on the basis of a light quantity having correlation with the molecularity, said instrument comprising theoretical light quantity calculation means for working out a theoretical light quantity per a single molecule, light quantity measurement means for measuring a light quantity of the sample by use of an image detector, and molecularity calculation means for working out the molecularity of the sample on the basis of a ratio of the light quantity of the sample to the theoretical light quantity as worked out.

With the molecularity measurement instrument, the molecularity of the sample is worked out on the basis of the ratio of the light quantity of the sample, as measured, to the theoretical light quantity as worked out, so that it is possible to derive the molecularity of the sample directly from the light quantity of the sample, the molecularity thereof being measured.

The invention is advantageous in that with the molecularity measurement method according to the invention, the molecularity of the sample is worked out on the basis of the ratio of the light quantity of the sample, as measured, to the theoretical light quantity as worked out, so that it is possible to derive the molecularity of the sample directly from the light quantity of the sample, the molecularity thereof being measured, and with the molecularity measurement instrument according to the invention, the molecularity of the sample is worked out on the basis of the ratio of the light quantity of the sample, as measured, to the theoretical light quantity as worked out, so that it is possible to derive the molecularity of the sample directly from the light quantity of the sample, the molecularity thereof being measured.

BRIEF DESCRIPTION OF THE DRAWINGS

FIG. 2 is a schematic representation showing a procedure for camera calibration;

FIG. 3 shows images read out by a camera by way of example;

DETAILED DESCRIPTION OF THE PREFERRED EMBODIMENTS

Embodiments of a molecularity measurement method according to the invention are described hereinafter with reference to FIGS. 1 to 5.

Embodiment 1

With the present embodiment, there is described hereinafter an example where the present invention is applied to "measurement of fluorescence molecularity distribution (fluorescence measurement) by means of a fluorescent light quantity".

Figure 1:
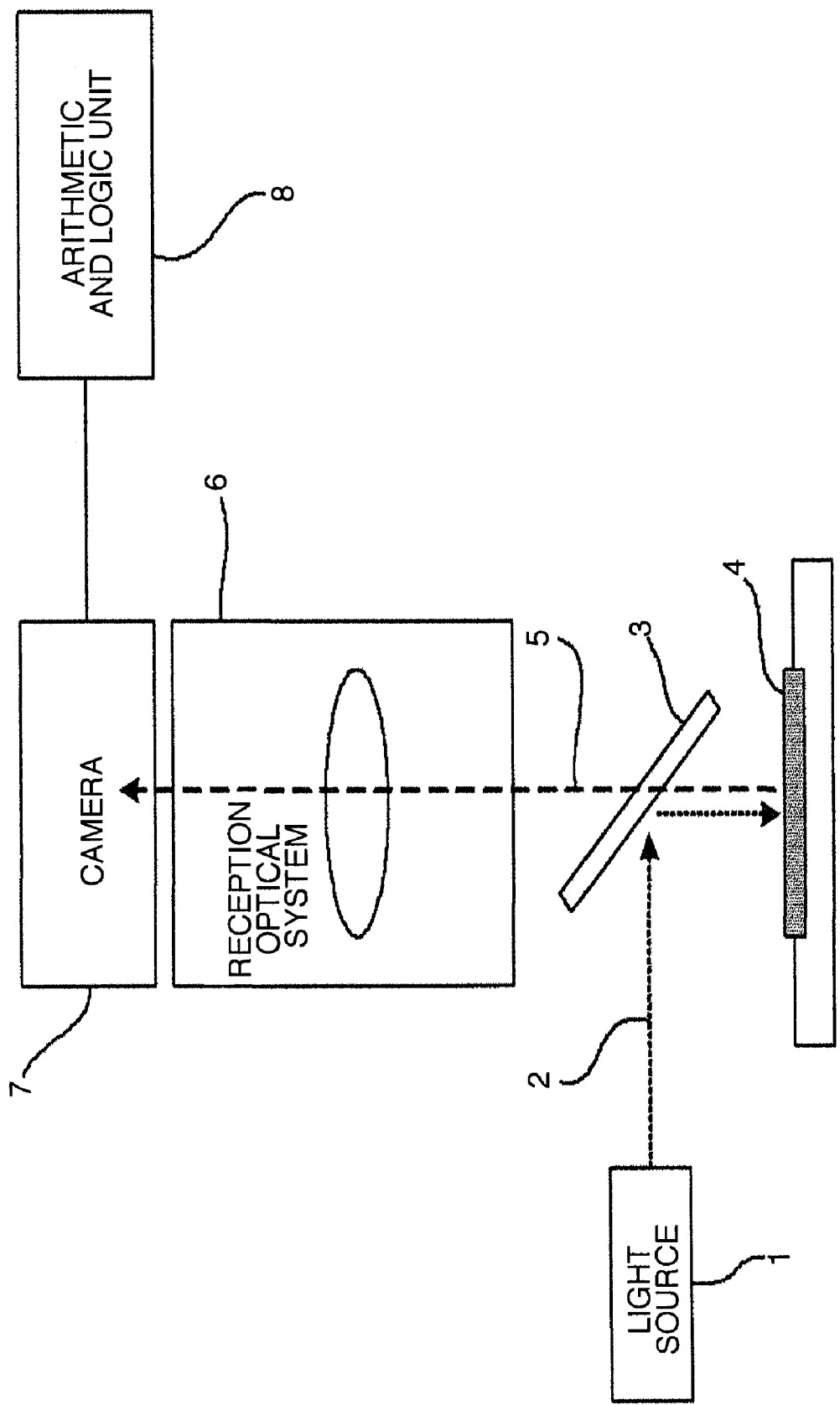
FIG. 1 is a schematic representation showing a configuration of an optical arrangement, and so forth, of a sample measurement system for executing fluorescence measurement.

FIG. 1 is a schematic representation showing a configuration of an optical arrangement, and so forth, of a sample measurement system for executing fluorescence measurement.

As shown in FIG. 1, excitation light from a light source 1 is reflected by a dichroic mirror 3 to thereby irradiate the whole region of a sample 4. Fluorescent light beam 5 from the sample 4 is transmitted through the dichroic mirror 3, falling on a reception optical system 6 to thereby form an image of the sample 4 on an image pickup face of a camera 7. Further, an arithmetic and logic unit 8 for executing a series of processes to be described later in the present description is connected to the camera 7. The arithmetic and logic unit 8 functions as theoretical light quantity calculation means, light quantity measurement means, and molecularity calculation means.

In the case of applying the molecularity measurement method according to the invention to the measurement of fluorescence molecularity distribution (the fluorescence measurement) by means of fluorescent light quantity, it is possible to measure a fluorescent light quantity on the sample, and spatial distribution of fluorescence molecularity by sequentially executing the following four steps. Further, "a measurement area" described hereunder is to indicate one unit of an area of spatial measurement in a direction orthogonal to an optical axis, such as one pixel of a camera, 1 $\mu m^2$, and so forth, as described later on.

a) Measurement of Camera Constant and an Excitation Light Quantity [W/m2] of a Sample Measurement is taken on camera factor [w·s/$m^2$/LSB] for use in the sample measurement system, and a measured value [W/m2] per unit area of excitation light with which the sample is actually irradiated, thereby preparing the sample measurement system.

b) Estimation on a Theoretical Fluorescent Light Quantity [w] of a Single Molecule "a theoretical fluorescent light quantity [w] of a single molecule" is estimated (calculated) on the basis of molar absorption coefficient $\epsilon$ of a fluorescent molecule as a measurement target, quantum efficiency, excitation wavelength efficiency, and the excitation light quantity [W/m2].

c) Measurement of a Fluorescent Light Quantity [w] Per a Measurement Area of a Sample "a fluorescent light quantity [w] per a measurement area of a sample" at a pixel as designated is measured on the basis of a pixel-read gradation value [LSB] of a camera actually picking up an image of the sample, elapsed time (s) for reading, and the camera factor [W·s/$m^2$/LSB]. The fluorescent light quantity represents a value traceable to the national standard.

d) Measurement on Sample Molecularity Per a Measurement Area

"sample molecularity per a measurement area" can be measured (estimated) by dividing "a fluorescent light quantity [w] per a measurement area of a sample" measured by a procedure under c) as above by "a theoretical fluorescent light quantity [w] of a single molecule" obtained by a procedure under b) as above.

In the case of fluorescence measurement, specific content of arithmetic operation is shown hereinafter.

a) Measurement on the Camera Factor and the Excitation Light Quantity [W/m2] of a Sample Measurement is taken on the camera factor [W·s/$m^2$/LSB] for use in the sample measurement system, and the measured value [W/m2] per unit area of excitation light with which the sample is actually irradiated, thereby preparing the sample measurement system.

a1) Decision on Camera Factor Kc by Calibration of a Camera

The camera factor Kc is the inherent calibration value of a camera, shown in JP 2004-191232A, varying in value according to measurement wavelength, but specific content thereof is not disclosed in JP 2004-191232A. The camera factor Kc is found by the following method. FIG. 2 is a schematic representation showing a procedure for camera calibration.

a1.1) Calibration of a Reference Light Emission Source

A light quantity is measured with a light quantity measuring instrument (power meter) for exclusive use.

As shown in FIG. 2, a reference light emission source 11 such as an LED, and so forth is first prepared, and the whole light quantity of the reference light emission source 11 is caused to fall on a power meter 12 traceable to the national standard through the reception optical system 6, thereby measuring the whole light quantity Is1 [W=J/s].

a1.2) Calibration of a Camera:

Subsequently, only the power meter 12 is replaced with the camera 7, and the whole light quantity of the reference light emission source 11 is caused to fall on the camera 7 similarly through the reception optical system 6. A read-value (gradation value) D[LSB] of the camera 7 is proportional to incident light quantity [W=J/s], and integral time t[s]. Herein, the gradation value D is expressed by an integer multiple of LSB (Least Significant Bit: least significant place bit at the time of A/D conversion), and in this case, 'LSB' is used as the unit of the gradation value. For example, all the gradation values of 16 bits are expressed by 0 to 65535LSB. Further, there are occasions when 'digit' is used as the unit of the gradation value.

Since the read-value (gradation value) D[LSB] of the camera 7 is proportional to the incident light quantity [W=J/s], and the integral time t[s] as described above, the quotient of the sum D1[LSB] of the gradation values divided by the integral time t1[s] of the camera will be proportional to the whole light quantity Is1[W]. In this case, conversion factor is designated K1.

$$Is1 = K1 \times D1/t1 \, [W = J/s]$$

Further, if magnitude of the reference light emission source 11 is defined as S1[m²], a light quantity per unit area can be defined as follows:

$$P1 = Is1/S1 \, [W/m2]$$

$$= K1 \times D1/t1/S1 \, [LSB/s/m^2]$$

Herein, the camera factor Kc is defined by the following formula:

$$Kc = K1/S1 \, [W \cdot s/m^2/LSB]$$

Accordingly, by use of Kc as above, the formula described previously is expressed by $$P1 = Kc \times D1/t1 \, [W/m2]$$

If the formula as above is generalized, the following holds:

$$Px = Kc \times D/t \, [W/m2] \quad (1)$$

where Kc: camera factor [W·s/m²/LSB],
t: elapsed time [s] at the time of measurement,
D: gradation value [LSB]

With the use of the formula (1), a light quantity value traceable to the national standard can be obtained out of the read-value of a camera. It is important to be able to obtain the value not as a simple value of [W] as in the case of an ordinary power meter, but as [W/m2].

FIG. 3 shows images read out by the camera by way of example. When the images shown in FIG. 3 are obtained, incident energy [W] is dependent on how many photons enter one pixel per a unit hour. Magnitude x (m) of one pixel at this point in time is also an important factor for determining the light quantity value.

That is, [1/m²] of the camera factor Kc means that the present measurement makes use of not only a function of the camera, for measuring a light quantity, but also a function for measuring "length" by the pixel.

Further, in the case of carrying out "measurement of light quantity distribution" as described later in the present description, it is necessary to ensure introduction of a concept of "light quantity value [W] per a measurement area (pixel, and so forth)". In such a case, energy [W] actually falling on one pixel can be worked out by multiplying [W/m2] obtained by the camera factor Kc, corresponding to "illuminance", by "an measurement area (pixel area, and so forth).

a 2) Measurement of Excitation Light

Excitation light is measured with the light quantity measuring instrument (power meter) for exclusive use.

Figure 4:
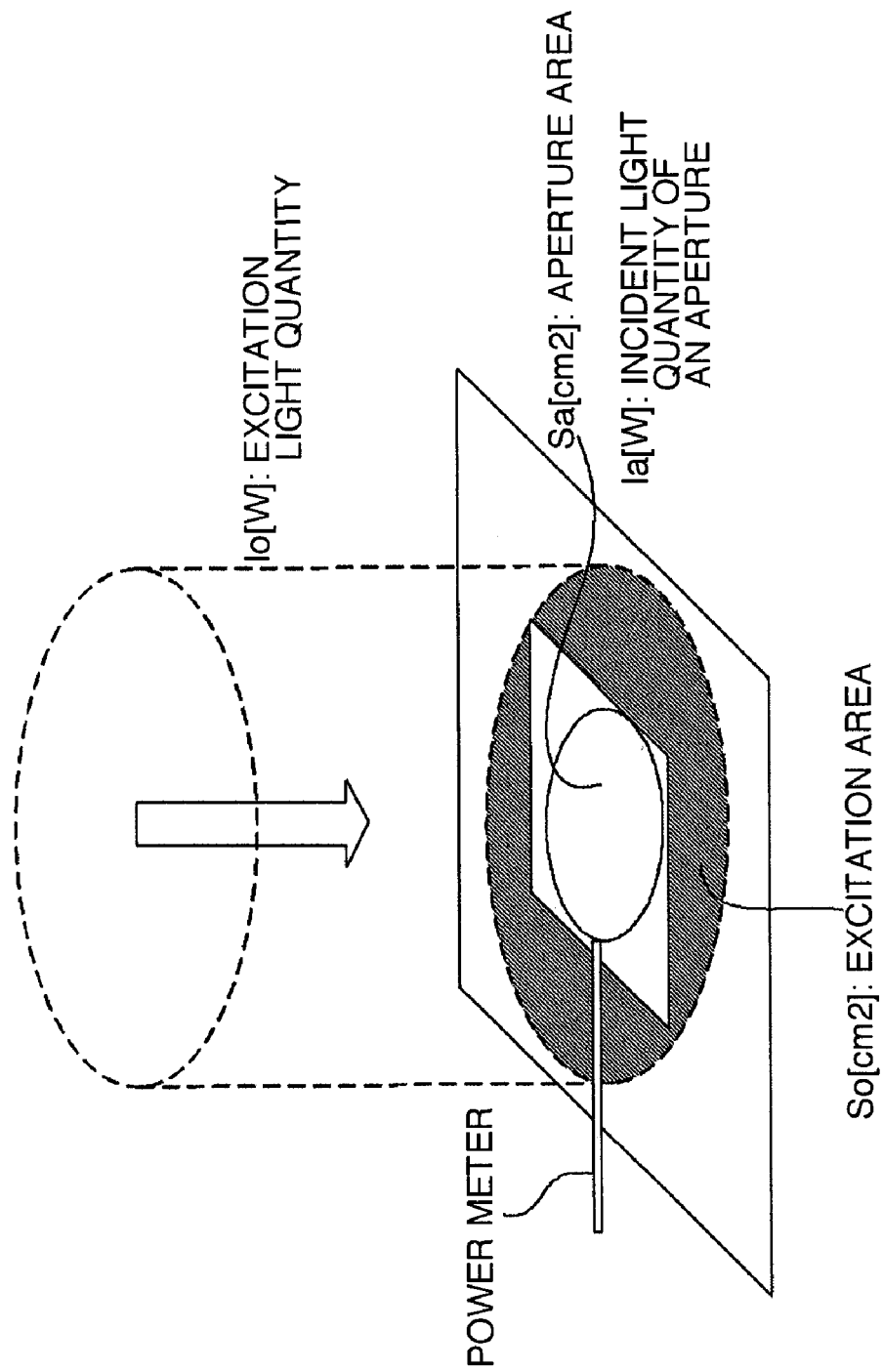
FIG. 4 is a schematic representation showing a concept on measurement of excitation light.

FIG. 4 is a schematic representation showing a concept on measurement of excitation light. A light receiver of the power meter is traced to the national standard, and total light quantity falling on an aperture of an incidence part thereof is measured on the basis of [W] unit. Accordingly, a measured light quantity $I_0$ is expressed as follows:

$$I_0 = (S_0/S_a) \times I_a \, [W] \quad (2)$$

where $I_a$ = incident light quantity of an aperture [W],
$S_a$ = aperture area [cm²]

Further, in order to execute accurate measurement, a measurement region of the excitation light is preferably in agreement with a region to be measured as much as possible.

b) Estimation on a Theoretical Fluorescent Light Quantity [W] Per a Measurement Area of a Single Molecule "a theoretical fluorescent light quantity [W] of a single molecule" is estimated (calculated) on the basis of molar absorption coefficient ε of a fluorescent molecule as a measurement target, quantum efficiency thereof, excitation wavelength efficiency thereof, and the excitation light quantity [W/m2].

b1) Estimation on an Absorption Light Quantity

In accordance with Lambert-Beer's law, an optical absorption quantity is expressed as follows:

$$\Delta I = 2.303 \times 10^3 \times \epsilon \times (I_0/S_0) \times n_0/N_A \, [W] \quad (3)$$

where $\Delta I$: optical absorption quantity [W], ε: molar absorption coefficient [M$^{-1}$cm$^{-1}$=L/mol/cm] ... common logarithm factor is used, $I_0$: excitation light quantity [W] @ $S_0$, $S_0$: excitation area [cm²], $n_0$: fluorescence molecularity in an excitation area, $N_A$: Avogadro number (6.0221415×10$^{23}$)

Herein, "a measurement area" is introduced. The measurement area refers to an area of a region the molecularity of which is to be evaluated, such as a pixel area of a camera, an area on a 1 μm² unit basis, and so forth. In the present description, the measurement area is expressed on a unit of [m²], but may be expressed on the basis of other units.

$S_m$: measurement area [m²]

With the present measurement, "fluorescence molecularity $n_m$" refers to molecularity per "a measurement area $S_m$".
$N_m$: fluorescence molecularity within a measurement area Meanwhile, absorption coefficient $\eta_a$[cm²] per a single molecule can be expressed as follows:

$$\eta_a = 2.303 \times 10^3 \times \epsilon/N_A \, [cm^2]$$

If formula (3) is replaced with the above, the following holds:

$$\Delta I = \eta_a \times (I_0/S_0) \times n_0 \, [W]$$

Now, "an optical absorption quantity $\Delta Pa$[W/m2] per a measurement area of $n_m$ pieces of fluorescent light molecules" is obtained by replacing $n_0$ in formula (3) with $n_m$ to be then divided by the measurement area $S_m$.

$$\Delta Pa = \eta_a \times (I_0/S_0) \times (n_m/S_m) \, [W/m2]$$

This indicates that an optical absorption quantity $\Delta Pa$[W/m2] per a measurement area, and a fluorescent light quantity will vary according to density ($n_m/S_m$) of fluorescent light molecules in the direction orthogonal to the optical axis, that is, depending on whether one fluorescent light molecule exists in 1 [m²] or 1[m²], and so forth even if the illuminance ($I_0/S_0$)[W/m2] of excitation light is the same.

In the case of $n_m = 1$ without the $S_m$, this will mean to assume only one molecule in the whole region irradiated with excitation light. In such a case, there is no assurance about in which of pixels photographed by the camera the one molecule will be photographed. As shown in formula (1), since the light quantity Px worked out by use of the camera factor Kc is expressed in terms of [W/m2], final calculation of $n_m$ is rendered easier by expressing the optical absorption quantity ΔPa as well in terms of [W/m2].

b2) Estimation on a Fluorescent Light Quantity

Figure 6:
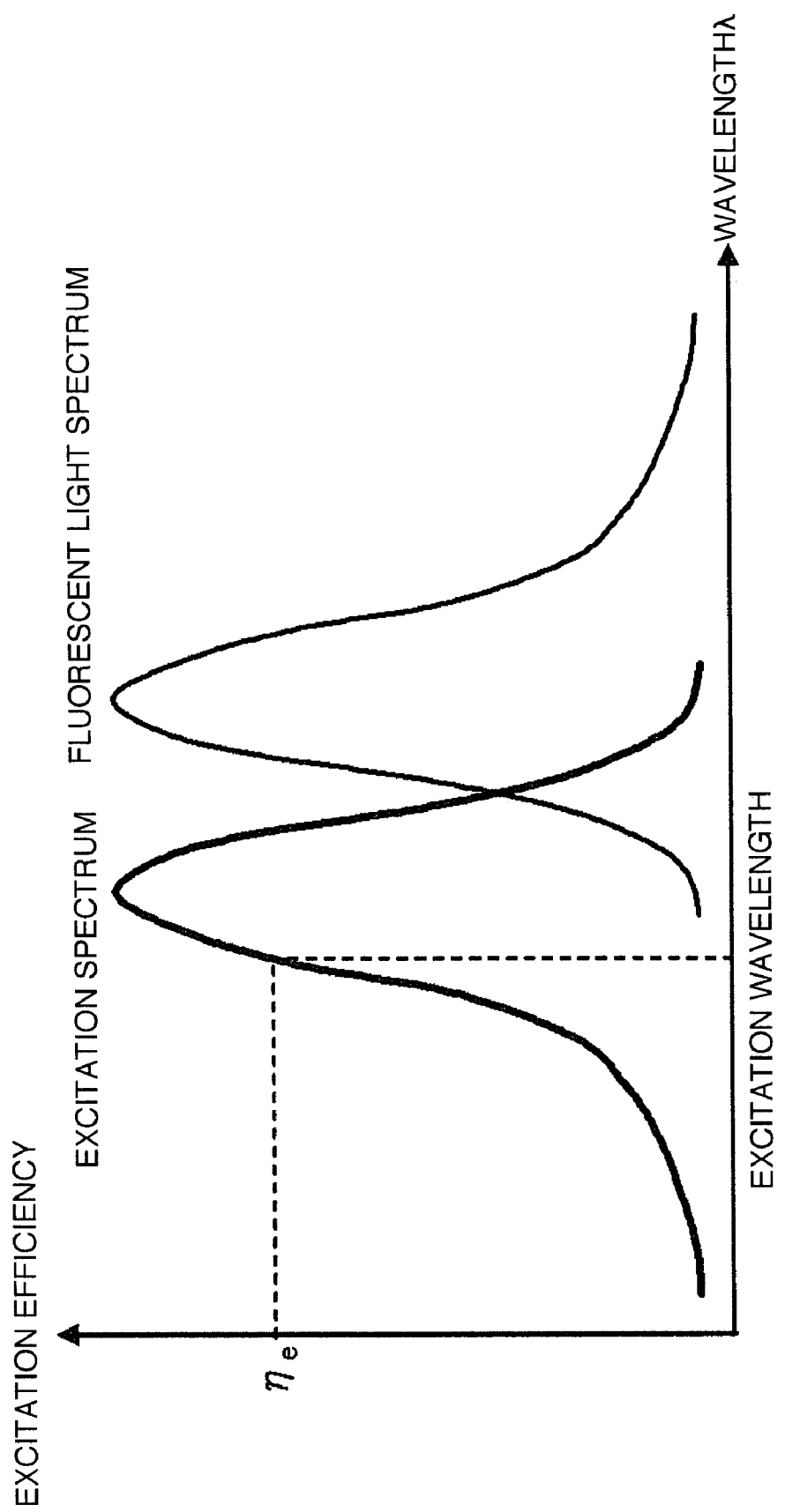
FIG. 6 is a graph showing excitation wavelength efficiency.

By adding the quantum efficiency of a fluorescent molecule, and so forth to the optical absorption quantity described in the foregoing, a theoretical fluorescent light quantity Pf[W/m2] can be expressed by the following formula:

$$Pf = \Delta Pa \times \eta_q \times \eta_e \times \eta_t [W/m2]$$

where $\eta_q$: quantum efficiency of a fluorescent molecule, $\eta_e$: excitation efficiency at an excitation wavelength of a fluorescent molecule (excitation wavelength efficiency ... FIG. 6), $\eta_t$: fluorescence wavelength transmission efficiency of a reception optical system.

A theoretical fluorescent light quantity Is of a single molecule in a measurement area is given as follows:

$$Is = (\Delta I/n_0) \times \eta_q \times \eta_e \times \eta_t [W] \qquad (4)$$

$$= \eta_a \times \eta_q \times \eta_e \times \eta_t (I_0/S_0)[W]$$

c) Measurement of a Fluorescent Light Quantity [W] Per a Measurement Area of a sample "a fluorescent light quantity [W] per a measurement area of a sample" at the pixel as designated is measured on the basis of the pixel-read gradation value [LSB] of the camera actually picking up the image of the sample, an elapsed time (s) for reading, and the camera factor [W·s/m²/LSB].

On the basis of formula (4), and by making use of the camera constant, a fluorescent light measured value $P_m$[W/m2] per a unit area of the sample can be expressed as follows:

$$P_m = Kc \times D/t [W/m2]$$

Herein, [1/m²] represents "a fluorescent light quantity per a unit area" by measurement of distance in a two-dimensional space, using the camera pixel.

For conversion of the fluorescent light quantity per a unit area into "a fluorescent light measured value $I_m$[W] per a measurement area", it will suffice to multiply the fluorescent light quantity per a unit area by the measurement area $S_m$.

$$I_m = Kc \times D/t \times S_m [W] \qquad (5)$$

where Kc: camera factor [W·s/m²/LSB],
t: elapsed time at the time of measurement [s],
D: gradation value [LSB]

d) Measurement on Sample Molecularity Per a Measurement Area

"sample molecularity per a measurement area" can be measured (estimated) by dividing "a fluorescent light quantity [W] per a measurement area of a sample" measured according to c) as above by "a theoretical fluorescent light quantity [W] of a single molecule" obtained according to b) as above.

"a theoretical fluorescent light quantity of a single molecule, per a measurement area" is expressed by formula (4) as follows:

$$I_s = \eta_a \times \eta_q \times \eta_e' \eta_t \times (I_0/S_0)[W]$$

The fluorescent light as measured is expressed by form a (5) as follows:

$$I_m = Kc \times D/t \times S_m [w]$$

Accordingly, estimated fluorescence molecularity $n_m$ can be expressed as follows:

$$n_m = I_m / I_s$$

$$= (Kc \times D/t) / \{\eta_a \times \eta_q \times \eta_e \times \eta_t \times (I_0/S_0)/S_m\}$$

$$= (Kc \times D \times S_0 \times S_m)/(t \times \eta_a \times I_0 \times \eta_q \times \eta_e \times \eta_t)$$

Further, in consideration of formula (2) expressed as follows:

$$I_0 = (S_0/S_a) \times I_a [W];$$

a measured value of an excitation light quantity $I_o$[W] is expressed as follows:

$$n_m = (Kc \times D \times S_a \times S_m)/(t \times \eta_a \times I_a \times \eta_q \times \eta_e \times \eta_t)$$

Since the transmission efficiency $\eta_t$ as well as the camera factor Kc of the measuring instrument is inherent in the instrument, those can be integrated as instrument constant Ki:

$$Ki = Kc/\eta_t$$

Further, a group of factors in the case where a fluorescent reagent serving as a target is decided upon can be integrated with the aperture area $S_a$ for measurement of excitation light into fluorescent light reception factor Ka as follows:

$$Ka = (Ki \times S_a)/(\eta_a \times \eta_q \times \eta_e)$$

In this case, the estimated fluorescence molecularity $n_m$ can be expressed simply as follows:

$$n_m = Ka \times D \times S_m/(I_a \times t)$$

Figure 5:
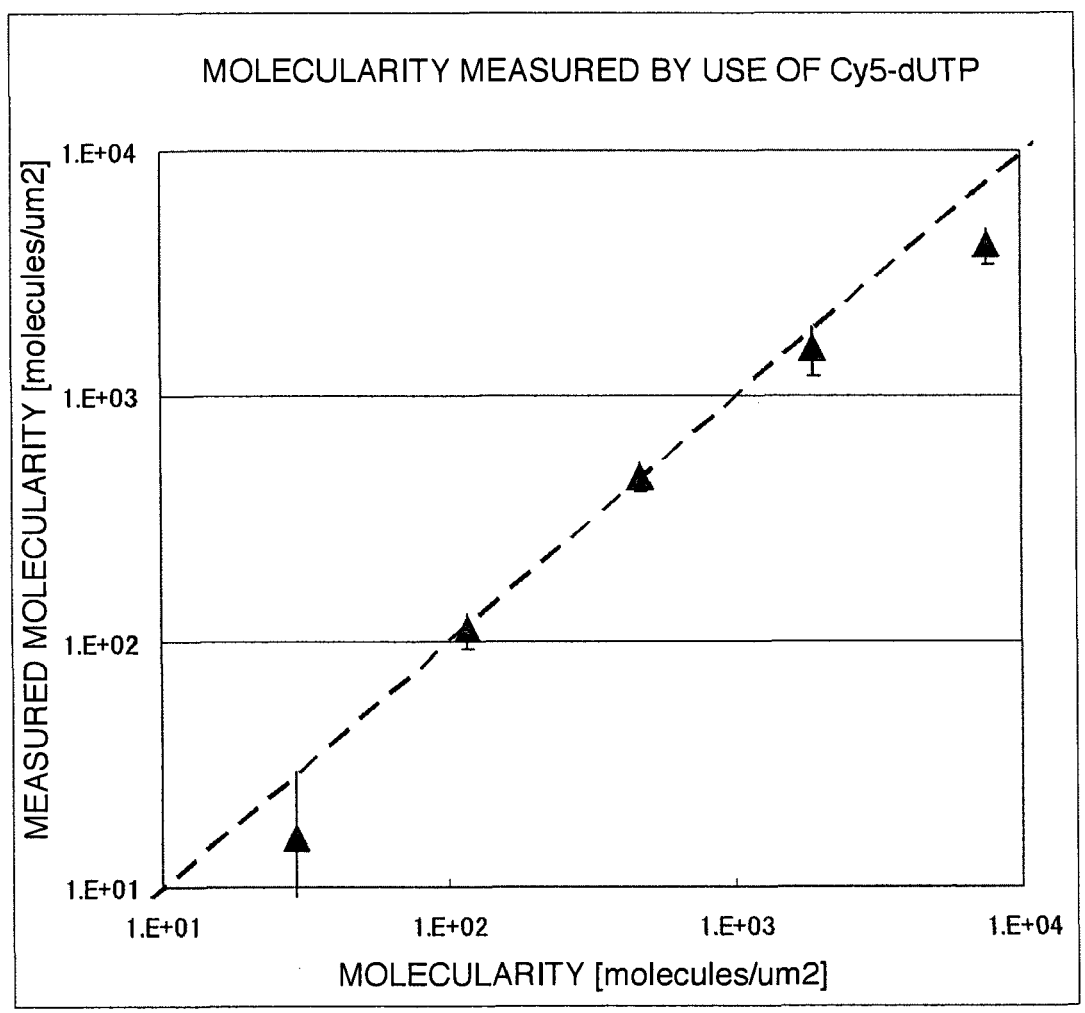
FIG. 5 is a graph showing molecularity measured by use of Cy5-dUTP.

FIG. 5 is a graph showing molecularity measured by use of the fluorescent reagent Cy5-dUTP (by GE Healthcare Corp.). In the figure, there is shown a case where UTP with Cy5 in various concentrations, added thereto, was spotted in the shape of a circle on a glass substrate, and fluorescence measurement was carried out by such a procedure as described above.

In this graph, a fluorescent light quantity corresponding to a spot is measured with a CCD camera, and molecularity worked out by conversion formulas described in the foregoing on the basis of the fluorescent light quantity is shown as measured molecularity along the vertical axis while shown along the horizontal axis is spot fluorescence molecularity, worked out on the basis of spot solution concentration on the substrate, spot quantity, and spot diameter. A broken line indicates respective theoretical values at which the spot fluorescence molecularity is in agreement with the measured molecularity.

As is evident from FIG. 5, with the adoption of a molecularity measurement method according to the invention, the theoretical value comes to sufficiently agree with the measured value.

With respect to the fluorescent light quantity, and so forth, only relative evaluation according to an optional unit system has been possible up to now, however, with the present invention, light quantity measurement by an absolute value traceable to the national standard having a unit of light quantity [W] is enabled by integrating those factors into two constants inherent in a sample measuring instrument, and one factor of an excitation (irradiation) light quantity measuring instrument. In so doing, it has become possible to make comparison between plurality of measurements in the same instrument, over time, and between measurements with respective bodies of different instruments.

The two constants inherent in the sample measuring instrument are Kc: the camera factor, and $\eta_t$ the fluorescence wavelength transmission efficiency of the reception optical system, and the one factor of the excitation (irradiation) light quantity measuring instrument is $S_a$: the aperture area (for measurement of excitation light).

Further, on the basis of a light quantity from a sample (fluorescent light, emission light, optical absorption), an excitation light quantity, and molecular constant, the number of molecules present in a sample can be measured (estimated) by the measurement area.

That is, assuming that the theoretical fluorescent light quantity per a single molecule is as follows:

$$I_s = \eta_a \times \eta_q \times \eta_e \times \eta_t \times (I_0/S_0)[W]$$

The measured fluorescent light quantity $P_m$ per a unit area of the sample is expressed as follows:

$$P_m = Kc \times D/t [W/m2]$$

Or, assuming that the fluorescent light quantity $I_m$ per the measurement area is expressed as follows:

$$I_m = Kc \times D/t \times S_m [w]$$

the fluorescence molecularity $n_m$ in the measurement area $S_m$ is shown as follows in either case:

$$n_m = (Kc \times D \times S_a \times S_m)/(t \times \eta_a \times I_a \times \eta_q \times \eta_e \times \eta_t)$$

In this connection, constants concerning fluorescent molecules (fluorescent reagent), necessary for calculation, are the following three:

$\epsilon$: molar absorption coefficient, $\eta_q$: quantum efficiency of a fluorescent molecule, $\eta_e$: excitation wavelength efficiency at an excitation wavelength of a fluorescent molecule Furthermore, if the present invention is applied to a two-dimensional image, this will enable not only information on a point in zero dimension but also a light quantity per each of pixels to be obtained from the two-dimensional image itself of a camera, so that it is possible to measure spatial distribution of fluorescence molecularities, in two-dimensions on a sample. By applying the present invention to, for example, the method disclosed in JP 2004-191232A, it is possible to measure spatial distribution of the fluorescence molecularities, in two-dimensions on a sample.

Further, by combining the present invention with a confocal optical system instead of an optical configuration such as a common microscope, and camera, [it is possible to measure spatial distribution of the fluorescence molecularities, not only in two-dimensions but also in three-dimensions.] it is possible to measure not only two-dimensional distribution of fluorescence molecularities on planes thereof but also three-dimensional distribution of fluorescence molecularities in spaces thereof.

Still further, application examples involving fluorescence can include the followings:

(1) With a DNA microarray comprising nucleic acid fixed onto a substrate thereof, it becomes possible to work out fluorescence molecularity of nucleic-acid subjected to hybridization. Further, if one fluorescent molecule is joined with one nucleic-acid molecule as a target for hybridization, it is possible to find out molecularity of a target nucleic-acid molecule as hybridized.

(2) By converting a signal of a DNA microarray after hybridization (hereinafter referred to as "hybri") into a light quantity [W], it becomes possible to make comparison in hybri-result between different platforms.

(3) By separately fixing fluorescent molecules identical in numbers to probe nucleic-acid molecules as spotted on a substrate, or nucleic-acid molecule with known fluorescence molecularity per a molecule on a substrate, it is possible to find out hybri-efficiency as reference. This is useful as means for compensation in case that color fading in fluorescent light poses a problem.

(4) In reaction such as binding of an acceptor in a cultured cell to a ligand, protein transfer on a filament in a cell, and so forth, if a known fluorescent molecule is kept in as-introduced state to thereby count the number of molecules in the cell, this will enable reaction within the cell to be quantitatively measured.

Embodiment 2

With Embodiment 1, fluorescence has been dealt with, however, the present invention can also be applied to molecular counting in "absorption" and "light emission". There is described hereinafter "measurement of optical absorption molecularity distribution by means of a transmission light quantity".

With the measurement of the optical absorption molecularity distribution by means of the transmission light quantity, spatial distribution of the optical absorption molecularity on a sample is measured in the following four steps:

a) Measurement of Camera Constant and an Excitation Light Quantity [W/m2] of a Sample Measurement is taken on camera factor [W·s/m²/LSB] for use in the sample measurement system, and a measured value [W/m2] per unit area of irradiation light with which the sample is actually irradiated, thereby preparing the sample measurement system.

b) Estimation on a Theoretical Optical Absorption Quantity [W] Per a Measurement Area of a Single Molecule "A theoretical optical absorption quantity [W] of a single molecule" per a measurement area is estimated on the basis of molar absorption coefficient $\epsilon$ of a molecule as a measurement target, absorption wavelength efficiency $\eta_e$, and irradiation light quantity [W/m2].

c) Measurement of an Optical Absorption Quantity [W] Per a Measurement Area of a Sample "An optical absorption quantity [W] per a measurement area of a sample" at a pixel as designated is measured on the basis of the measured value [W/m2] per unit area of the irradiation light with which the sample is actually irradiated, a pixel-read gradation value [LSB] of a pixel of the camera actually picking up the image of the sample, the elapsed time (s) for reading, and the camera factor [w·s/m²/LSB]. In optical absorption measurement, an irradiation light quantity, in a state without a sample in presence, is measured before, or after measurement of the sample, thereby defining the irradiation light quantity as 100%. Herein, attenuation in light quantity, found out after the measurement of the sample, represents an optical absorption quantity.

d) Measurement on Sample Molecularity $n_m$ Per a Measurement Area

"sample molecularity $n_m$ per a measurement area" can be measured (estimated) by dividing "an optical absorption quantity [W] per a measurement area of a sample" measured according to c) as above by "a theoretical optical absorption quantity [W] of a single molecule" obtained according to b) as above.

Embodiment 3

Next, there is described hereinafter an example wherein the present invention is also applied to molecular counting in "light emission".

There is described hereinafter "measurement of light emission molecularity distribution by means of an emission light quantity".

With the measurement of the light emission molecularity distribution by means of the emission light quantity, spatial distribution of the light emission molecularity on a sample is measured in the following three steps:

a) Measurement of Camera Constant and an Excitation Light Quantity [W/m2] of a Sample Measurement is taken on camera factor [W·s/m²/LSB] for use in the sample measurement system, thereby preparing the sample measurement system.

b) Estimation on a Theoretical Emission Light Quantity [W] Per a Measurement Area of a Single Molecule "A theoretical emission light quantity [W] of a single molecule" per a measurement area is estimated on the basis of luminous efficiency of a light-emitting molecule as a measurement target, input energy efficiency $\eta_e$ for ATP and so forth, and a measured value [W] of energy actually consumed in a sample.

c) Measurement of an Emission Light Quantity [W] Per a Measurement Area of a Sample "An emission light quantity [W] per a measurement area of a sample" at a pixel as designated is measured on the basis of a pixel-read gradation value [LSB] of a pixel of the camera actually picking up the image of emission light of the sample, the elapsed time (s) for reading, and the camera factor [W·s/m²/LSB].

d) Measurement on Sample Molecularity Per a Measurement Area

"sample molecularity per a measurement area" can be measured (estimated) by dividing "an emission light quantity [W] per a measurement area of a sample" measured according to c) as above by "a theoretical emission light quantity [Ww] of a single molecule" obtained according to b) as above.

Reaction of a firefly-luciferin-luciferase light emission system cited as an example of light emission is reaction whereby D-luciferin as matrix is converted in the presence of ATP and $Mg^{2+}$ into oxiluciferin that is an emitter by the agency of luciferase.

Embodiment 4

Next, there is described hereinafter an example wherein the present invention is applied to "measurement of an emission light quantity of a single molecule with respect to a light-emitting molecule".

It is difficult to carry out a measurement on the luminous efficiency $\epsilon$ of the light-emitting molecule, and the input energy efficiency $\eta_e$ for ATP and so forth, shown with reference to Embodiment 3. In contrast, with the present embodiment, "a theoretical emission light quantity [W] of a single molecule" is measured in the following three steps. In addition, by taking into account external energy such as ATP, and so forth, to be separately added, it is possible to estimate the luminous efficiency $\epsilon$ and the input energy efficiency $\eta_e$ for ATP and so forth. This procedure is shown in the following four steps:

a) Measurement of Camera Constant and an Excitation Light Quantity [W/m2] of a Sample Measurement is taken on camera factor [W·s/m²/LSB] for use in the sample measurement system, thereby preparing the sample measurement system.

b) Measurement on Sample Molecularity Per a Measurement Area

"sample molecularity per a measurement area" is measured on the basis of a method according to Embodiment 2 (the case of the known absorption coefficient), or sample weight, and molecular weight of a single molecule.

c) Measurement of an Emission Light Quantity [w] Per a Measurement Area of a Sample "An emission light quantity [W] per a measurement area of a sample" at a pixel as designated is measured on the basis of a pixel-read gradation value [LSB] of a pixel of the camera actually picking up the image of emission light of the sample, elapsed time(s) for reading, and the camera factor [W·s/m²/LSB].

d) Measurement of a Theoretical Emission Light Quantity [W] Per a Measurement Area of a Single Molecule "A theoretical emission light quantity [W] of a single molecule" per a measurement area is measured (estimated) by dividing "an emission light quantity [W] per a measurement area of a sample" measured according to c) as above by "sample molecularity $n_m$ per a measurement area" according to b) as above. Furthermore, if the external energy such as ATP, and so forth, to be added, is divided by molecularity, this will enable the input energy efficiency $\eta_e$ such as emission coefficient $\epsilon$ per a single molecule, and so forth to be estimated.

As described in the foregoing, with the molecularity measurement method according to the invention, it is possible to derive the emission coefficient $\epsilon$ of a sample, and the input energy efficiency $\eta_e$ directly from a light quantity of the sample with measured molecularity on the basis of a ratio of a measured light quantity of the sample to a theoretical light quantity as worked out.

It is to be understood that an application range of the invention is not limited to those embodiments described in the foregoing. The invention is extensively applicable to a molecularity measurement instrument for quantitatively measuring molecularity of a sample on the basis of a light quantity having correlation with the molecularity, and a molecularity measurement method using the same.

What is claimed is:

1. A molecularity measurement method for quantitatively measuring molecularity of a sample on the basis of a light quantity having correlation with the molecularity, said method comprising the steps of:
   working out a theoretical light quantity per a single molecule;
   measuring a light quantity of the sample by use of an image detector; and
   working out the molecularity of the sample on the basis of a ratio of the light quantity of the sample to the theoretical light quantity as worked out.

2. The molecularity measurement method according to claim 1 further comprising the step of calibrating corresponding relationship between a light quantity of the image detector, and an output value thereof, and in the step of measuring the light quantity of the sample, the light quantity of the sample is measured by use of the corresponding relationship as calibrated.

3. The molecularity measurement method according to claim 1, wherein the light quantity having the correlation with the molecularity is a fluorescent light quantity of fluorescence emitted from the sample, and in the step of working out the theoretical light quantity, a theoretical fluorescent light quantity is worked out as the theoretical light quantity by use of molar absorption coefficient, quantum efficiency, excitation wavelength efficiency, and an excitation light quantity.

4. The molecularity measurement method according to claim 1, wherein the light quantity having the correlation with the molecularity is an optical absorption quantity by the sample.

5. The molecularity measurement method according to claim 1, wherein the light quantity having the correlation with the molecularity is an emission light quantity.

6. The molecularity measurement method according to claim 1, wherein the image detector comprises a confocal optical system.

7. A molecularity measurement instrument for quantitatively measuring molecularity of a sample on the basis of a light quantity having correlation with the molecularity, said instrument comprising:

theoretical light quantity calculation means for working out a theoretical light quantity per a single molecule;

light quantity measurement means for measuring a light quantity of the sample by use of an image detector; and molecularity calculation means for working out the molecularity of the sample on the basis of a ratio of the light quantity of the sample to the theoretical light quantity as worked out.

* * * * *